(12) United States Patent
Kim (10) Patent No.: US 8,293,267 B2
(45) Date of Patent: Oct. 23, 2012

(54) METHOD FOR PREPARING AN ANTIMICROBIAL COTTON OF CELLULOSE MATRIX HAVING CHEMICALLY AND/OR PHYSICALLY BONDED SILVER AND ANTIMICROBIAL COTTON PREPARED THEREFROM

(75) Inventor: Ju Young Kim, Tallahassee, FL (US)

(73) Assignee: AG Biotech, LLC, Tallahassee, FL (US)

( * ) Notice: Subject to any disclaimer, the term of this patent is extended or adjusted under 35 U.S.C. 154(b) by 343 days.

(21) Appl. No.: 12/456,162

(22) Filed: Jun. 12, 2009

(65) Prior Publication Data

US 2010/0316693 A1 Dec. 16, 2010

(51) Int. Cl.
*A61K 9/00* (2006.01)
*A61K 9/70* (2006.01)
*A61K 31/28* (2006.01)
*A61K 33/38* (2006.01)

(52) U.S. Cl. ........ 424/443; 424/485; 424/488; 424/618; 514/495

(58) Field of Classification Search .................. 424/443, 424/485, 488, 618; 514/495
See application file for complete search history.

(56) References Cited

U.S. PATENT DOCUMENTS

| | | | |
|---|---|---|---|
| 4,977,892 A | 12/1990 | Ewall | |
| 7,267,828 B2 | 9/2007 | Parsons et al. | |
| 2003/0147960 A1* | 8/2003 | Lin et al. | 424/486 |
| 2010/0112884 A1* | 5/2010 | Tsai | 442/123 |

FOREIGN PATENT DOCUMENTS

KR 20030070038 A 8/2003

* cited by examiner

*Primary Examiner* — Mina Haghighatian
(74) *Attorney, Agent, or Firm* — The Webb Law Firm

(57) ABSTRACT

There is provided a method for preparing a natural cellulose-OAg matrix having antimicrobial activity without leaching silver from the cellulose-OAg matrix. The method comprises: introducing silver ions ($Ag^+$) into a natural cellulose matrix by dipping the natural cellulose matrix in an AgCl-dissolved $NH_4OH$ solution; and substituting hydrogen (H) of hydroxyl group (—OH) in natural cellulose with $Ag^+$ by drying the silver ion-infused natural cellulose matrix, thus to form a natural cotton-OAg complex. The cellulose-OAg matrix prepared in the method may be useful to continuously maintain antimicrobial activity by maintaining an effective concentration of silver, which does not have cytotoxicity to human skin, and chemically bonded silver is not leached during the rehydration due to the chemical bond between the silver and the cellulose matrix.

16 Claims, 4 Drawing Sheets
(1 of 4 Drawing Sheet(s) Filed in Color)

METHOD FOR PREPARING AN ANTIMICROBIAL COTTON OF CELLULOSE MATRIX HAVING CHEMICALLY AND/OR PHYSICALLY BONDED SILVER AND ANTIMICROBIAL COTTON PREPARED THEREFROM

TECHNICAL FIELD

The present invention relates to an antimicrobial cotton having chemically and/or physically bonded silver and a method for preparing the same, and more particularly, to a method for preparing a natural cellulose matrix having chemically bonded silver by introducing silver ions ($Ag^+$) into a natural cellulose matrix and drying the natural cellulose matrix to form a cellulose-OAg complex.

BACKGROUND ART

Silver is the $68^{th}$ most abundant element in the earth's crust, and has been used in a variety of applications from currency to semiconductors. In particular, silver has been used as one of the precious metals such as gold and platinum from old times. The precious metals are metals having the lowest side effects to the skin of humans and animals when they are in contact. Among them, silver has been used in a wide variety of applications such as the treatment of skin diseases and medical services since silver is known to be a heavy metal that has antimicrobial activity and is not harmful to human beings.

In order to employ the antimicrobial activity of silver to kill a variety of harmful microorganisms, antimicrobial fibers, which were obtained by physically binding silver to cellulose, latex, polyethylene, polypropylene and the like, have been widely used in the medical field. In addition, silver-infused bandages have the ability to kill bacteria, fungi, protozoa and virus and thus protect wounds from them. Most of the silver-infused bandages such as silver dressing materials are associated with burn patients. For example, it was reported that, when a silver-infused bandage is applied to burn patients, the regeneration of the damaged skin is facilitated by various factors.

In addition, device-associated infections come with a heavy burden in clinical and economic terms. For example, it takes at least $2,836 per infection to manage catheter-associated bacteremia.

In recent years, silver is most commonly applied to a dressing material for treating a wound and a central venous catheter. An anesthetic (silver sulfadiazine and chlorhexidine) central venous catheter has the effect of reducing the bacterial infection, compared to the control catheters. In the field of medical services, another use of silver is preparing a silver protein that is used to treat conjunctivitis of eyes.

Silver is mainly used to prevent bacterial infection. It was shown that silver dressing materials for treating a wound may contribute meaningfully to the field of medical services. When silver is used as a dressing material for treating a wound, the results revealed that the silver is very harmful to fibroblast cells.

The most important, recently used silver compounds include silver sulfadiazine (AgSD), metallic silver, silver acetate, and silver protein. These silver compounds are used to prevent infection in burned skin and ocular diseases and to eradicate warts, but silver has problems associated with cytotoxicity. In recent years, a bandage is treated with silver nitrate to obtain a silver-infused bandage. However, this silver-infused bandage still has problems associated with cytotoxicity to skin cells and silver leaching.

On the grounds as described above, it is necessary to permanently infuse silver into cellulose. The present invention's technology of permanently fixing silver in the cellulose is useful to apply to cellulose fibers or cotton, and is required in a large number of applications including wood preservation, antibiotic bandages, water purification, and other possibilities.

DISCLOSURE

Technical Problem

An aspect of the present invention provides a method for preparing a natural cellulose matrix having chemically bonded silver, or chemically and physically bonded silver, wherein the natural cellulose matrix has antimicrobial activity, and bonds of silver maintain silver content sufficient to keep antimicrobial activity during rehydration; and a natural cellulose matrix having bonded silver prepared therefrom.

Another aspect of the present invention provides a method for preparing a cellulose matrix having bonded silver, wherein the cellulose matrix has antimicrobial activity and shows low or no cytotoxicity to the human skin, and silver is not leached from the cellulose matrix during rehydration; and a natural cellulose matrix having bonded silver prepared therefrom.

SUMMARY OF THE INVENTION

These aspects and other aspects of the present invention may be achieved with reference to the following exemplary embodiments of the present invention.

According to an aspect of the present invention, there is provided a method for preparing an antimicrobial cotton of natural cellulose matrix having bonded silver. Here, the method comprises: introducing silver ions ($Ag^+$) into a natural cellulose matrix by dipping the natural cellulose matrix in an AgCl-dissolved $NH_4OH$ solution; and substituting hydrogen (H) of hydroxyl group (—OH) in cellulose with $Ag^+$ by drying the silver ion-infused natural cellulose matrix, thus forming a cellulose-OAg complex having a chemical bond.

In this case, the concentration of silver in the $NH_4OH$ solution may be in the range of 0.00035 to 0.0035 w/v %.

According to another aspect of the present invention, there is provided a method for preparing an antimicrobial cotton of natural cellulose matrix having chemically and/or physically bonded silver. Here, the method comprises: introducing silver ions ($Ag^+$) into a natural cellulose matrix by dipping the natural cellulose matrix in an AgCl-dissolved $NH_4OH$ solution; and substituting hydrogen (H) of hydroxyl group (—OH) in cellulose with $Ag^+$ by drying the silver ion-infused natural cellulose matrix, thus to form a chemical bond of a cellulose-OAg complex and a physical bond between cellulose and silver molecules or particles of silver oxide ($Ag_2O$).

In this case, the concentration of silver in the $NH_4OH$ solution may be in the range of 0.0035 to 7.5 w/v %.

According to still another aspect of the present invention, there is provided an antimicrobial cotton of natural cellulose matrix having chemically and/or physically bonded silver, wherein the natural cellulose matrix is prepared in the method as described above, and has a chemical bond of a cellulose-OAg complex, or a chemical bond of a cellulose-OAg complex and a physical bond between particles of silver oxide ($Ag_2O$) and cellulose, the cellulose-OAg complex being formed by substituting hydrogen (H) of hydroxyl group (—OH), which is present in the $3^{rd}$ carbon of glucose units, with $Ag^+$ by drying the silver ion-infused natural cellulose matrix.

As described above, the antimicrobial, natural cellulose matrix having bonded silver according to one exemplary embodiment of the present invention may be useful to maintain the antimicrobial activity semi-permanently since silver chemically bonded to the cellulose matrix is present in a higher concentration than required to show antimicrobial activity although small amounts of non-reacted silver and physically bonded silver may leach from the cellulose matrix when physical forces such as washing are applied to the cellulose matrix, or during the rehydration.

Also, the antimicrobial, natural cellulose matrix having chemically bonded silver according to one exemplary embodiment of the present invention has low or no cytotoxicity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Hereinafter, exemplary embodiments of the present invention will be described in more detail.

The method for preparing a natural cellulose matrix having bonded silver according to one exemplary embodiment of the present invention comprises: introducing silver ions ($Ag^+$) into a natural cellulose matrix by dipping the natural cellulose matrix in an AgCl-dissolved $NH_4OH$ solution; and substituting hydrogen (H) of hydroxyl group (—OH) in cellulose with $Ag^+$ by drying the silver ion-infused natural cellulose matrix, thus to form a cellulose-OAg complex having a chemical bond and a physical bond between cellulose and silver molecules.

In the present invention, natural cellulose is used as the cellulose matrix. This cellulose is one of organic media that occur spontaneously, and are nontoxic and biodegradable, and have a huge pelletized surface area. Therefore, it is ideal to apply to the field of environmental and medical services. Cellulose may be obtained from various sources of supply including woody plants and non-woody plants, but the present invention is not particularly limited thereto.

Silver is preferably supplied in the form of AgCl, which is used as the silver compound, and $NH_4OH$ is preferably used as the solvent. When $NH_4OH$ reacts with AgCl, other residual compounds are not formed except for $NH_4Cl$ that is unharmful to human beings. Therefore, the use of $NH_4OH$ is particularly preferred. First, AgCl is dissolved by reaction with $NH_4OH$, and the dissolved silver ions then bind to a cellulose matrix. In this case, the $NH_4OH$ is released in a gaseous form such as $NH_3$ and the pH of the reaction solution is reduced to a neutral pH when the reaction is completed. When other alkaline substances are used instead of the $NH_4OH$, AgCl is not dissolved in water, and reacts with the alkaline substances to form by-products. Therefore, it is undesirable to use other alkaline substances.

AgCl used as the silver compound is dissolved by reaction with $NH_4OH$, as represented by the following Equation 1.

$$AgCl + 2(NH_4OH) = [Ag(NH_3)_2]Cl + 2H_2O \qquad \text{Equation 1}$$

In general, since a hydroxyl group present in C-3 of the glucose unit has the highest acidity among three hydroxyl groups of the cellulose, $H^+$ is released from an alcohol group (R—OH) of the cellulose to form a radical (R—O$^-$) in an alkoxylate form. Here, the radical (R—O$^-$) of the cellulose reacts with silver, which allow the silver to chemically bind to the cellulose. A possible binding mode between Ag+ and cellulose is represented by the following Formula 1.

Formula 1

One ionic silver molecule may have up to four ligands, and hydroxyl groups in C-2 and C-3 of glucose unit may bind to metal ions in a bidentate form. Thus, the hydroxyl group in the C-3 of the glucose unit has the highest acidity among three hydroxyl groups of the glucose unit. Then, it is considered that one of the hydroxyl groups in the cellulose binds to silver in an alkoxylate form. These hydroxyl groups effectively react with silver ions to form chelate compounds, which, in turn, prevents the metal ions from being leached in an aqueous solution.

This reaction is achieved by substituting hydrogen (H) of hydroxyl group (—OH) in cellulose with $Ag^+$ by drying the silver ion-infused cellulose matrix, thus to form a cellulose-OAg complex. Then, the cellulose reacts with silver ions to form chelate compounds, which, in turn, prevents the silver ions from being leached even in an aqueous solution.

The reaction is preferably carried out for 1 to 96 hours. When the reaction is carried out for 1 hour or less, AgCl is not sufficiently dissolved in an $NH_4OH$ solution, the $NH_4OH$ solution may be discolored by oxidation of non-reacted AgCl after the reaction with the cellulose, and silver may insufficiently bind to the cellulose matrix, which makes it impossible to achieve the sufficient effects according to the present invention. When the reaction time exceeds 96 hours, AgCl is not dissolved further, but silver particles are formed. The reaction time may be more preferably in a range of 3 to 48 hours, and still more preferably in a range of 5 to 24 hours.

The above-mentioned cellulose-OAg complex is formed in the cellulose matrix prepared in the method according to one exemplary embodiment of the present invention, that is, silver chemically binds to cellulose. In addition to the chemical binding of the silver, the silver physically binds to the cellulose, that is, the silver is present in the cellulose in the form of $Ag_2O$, Ag and AgCl. The reaction where the silver chemically binds to the cellulose to form a cellulose-OAg complex is carried out in a $NH_4OH$ solution where the concentration of silver is 0.0035 w/v%. Here, when the concentration of silver falls below this range, the physical binding of the silver seems not to occur.

Then, the cellulose matrix is dried, and then washed to remove silver ions, AgCl and by-products in the form of particles that are not physically and chemically bound.

In this case, a drying temperature is preferably in a range of 100 to 150° C., but the present invention is not particularly limited thereto. When Ag in the cellulose matrix is present in the form of AgO or $Ag_2O$, the cellulose matrix maintains its white color. Here, when the cellulose matrix is dried in the temperature range, Ag physically binding to the cellulose matrix may be converted into $Ag_2O$ or AgO so as to maintain its white color, and thus to show more potent antimicrobial activity.

Although the cellulose-OAg complex having chemically bonded silver prepared by the above-mentioned method according to one exemplary embodiment of the present invention is dispersed in water, Ag is sparingly leached from the cellulose-OAg complex, as the physically bonded silver ions are not detached from the cellulose-OAg complex when a physical force is applied.

The leaching of Ag is distinguished from the case where the silver present in the $NH_4OH$ solution does not chemically or physically bind to natural cellulose or where the silver is lost as the cellulose-OAg complex is worn away by abrasion.

The cellulose-OAg complex is formed by the chemical binding of silver to the cellulose matrix. As a result, the cellulose-OAg complex is endowed with antimicrobial activity. A concentration of silver in the matrix, which is sufficient for showing the antimicrobial activity, is approximately 0.01 mg/g. This antimicrobial activity may be achieved using an $NH_4OH$ solution in which silver is present in a concentration of 0.00035 w/v% or more. When the silver concentration in the $NH_4OH$ solution is less than this amount, the silver chemically or physically binding to the cellulose matrix does not show sufficient antimicrobial activity.

The antimicrobial activity is improved with an increasing concentration of silver. However, when the concentration of silver exceeds 7.5 w/v %, it is undesirable for economic reasons and due to the limitation on the solubility of AgCl in the $NH_4OH$ solution.

Meanwhile, when silver is present in an excessive concentration, the silver may be toxic to human cells. Therefore, it is preferable not to exceed an optimum concentration of silver when used in articles that are in direct contact with human skin for an extended time period. That is, when the concentration of silver in the matrix exceeds approximately 1.0 mg/g, the toxicity to human cells does not seriously damage human bodies, but the cytotoxicity gradually starts to appear. The matrix having sufficient concentration of silver to show this cytotoxicity is realized in the use of an $NH_4OH$ solution including 0.035 w/v % of silver. However, when the concentration of silver in the $NH_4OH$ solution exceeds 0.35 w/v %, the silver is strongly cytotoxic to human cells, thereby undesirably affecting human bodies. Therefore, it is preferred to limit the concentration of silver to 0.35 w/v % or less.

Therefore, the concentration of silver in the $NH_4OH$ solution, which is suitable for preparing a cellulose matrix having the antimicrobial activity, is preferably in a range of 0.00035 to 7.5 w/v %. In addition, when the silver is used in articles that are in direct contact with the human body, the silver should show sufficient antimicrobial activity and have no cytotoxicity. Therefore, the concentration of silver is preferably in a range of 0.00035 to 0.35 w/v %.

The natural cellulose matrix such as cotton as prepared according to the present invention may be used in various applications including medical articles such as a bandage and a gauze that are applied to the affected part; articles such as socks, towels, clothing and masks that are in direct contact with human body; textile articles such as bedcovers that are made from cotton, and the like, but the present invention is not particularly limited thereto. Therefore, the natural cellulose matrix according to the present invention may be useful to provide bactericidal and antibiotic properties to articles or skin that is in direct contact with the articles, and also to have the effect of treating atopic dermatitis. Also, the natural cellulose matrix according to the present invention may be widely used in various applications requiring antimicrobial activity, such as antibacterial filters used in water purifiers or air cleaners, etc.

Hereinafter, exemplary embodiments of the present invention are described in more detail. However, it is considered that the description proposed herein is just a preferable example for the purpose of illustration only, not intended to limit the scope of the invention.

EXAMPLES

A complex of a natural cellulose matrix having bonded silver was prepared, and the natural cellulose matrix thus prepared was tested for leaching ratio, antibiotic effect, and cytotoxicity to human alveolar epithelial cells.

1. Preparation of Silver-Cellulose Matrix Complex Formation of Oral Cotton Pellet An oral cotton pellet was formed by processing natural cotton into pellet and slightly coating the surface of the pellet with edible sodium carboxymethyl cellulose (Na-CMC).

Formation of cellulose-OAg complex for oral cotton pellet

Next, 10, 5, 0.5, 0.05, 0.005 and 0.0005 g of AgCl were dissolved in an $NH_4OH$ solution under atmospheric conditions, so that the concentration of silver can be adjusted to 7.5, 0.75, 0.35, 0.035, 0.0035 and 0.00035 w/v %, respectively. Then, the oral cotton pellets were added respectively to the resulting solutions to allow a cellulose matrix of cotton to react with silver, thus to form cellulose-OAg complexes. In this case, the reactions were carried out for 24 hours.

After the reaction, the cellulose-OAg complexes were washed three times with water, and then dried. In this case, the pH of the cellulose-OAg complexes was in a range of 6 to 8, the reactions were carried out at room temperature, and the drying temperature was not greater than 105° C.

Figure 1:
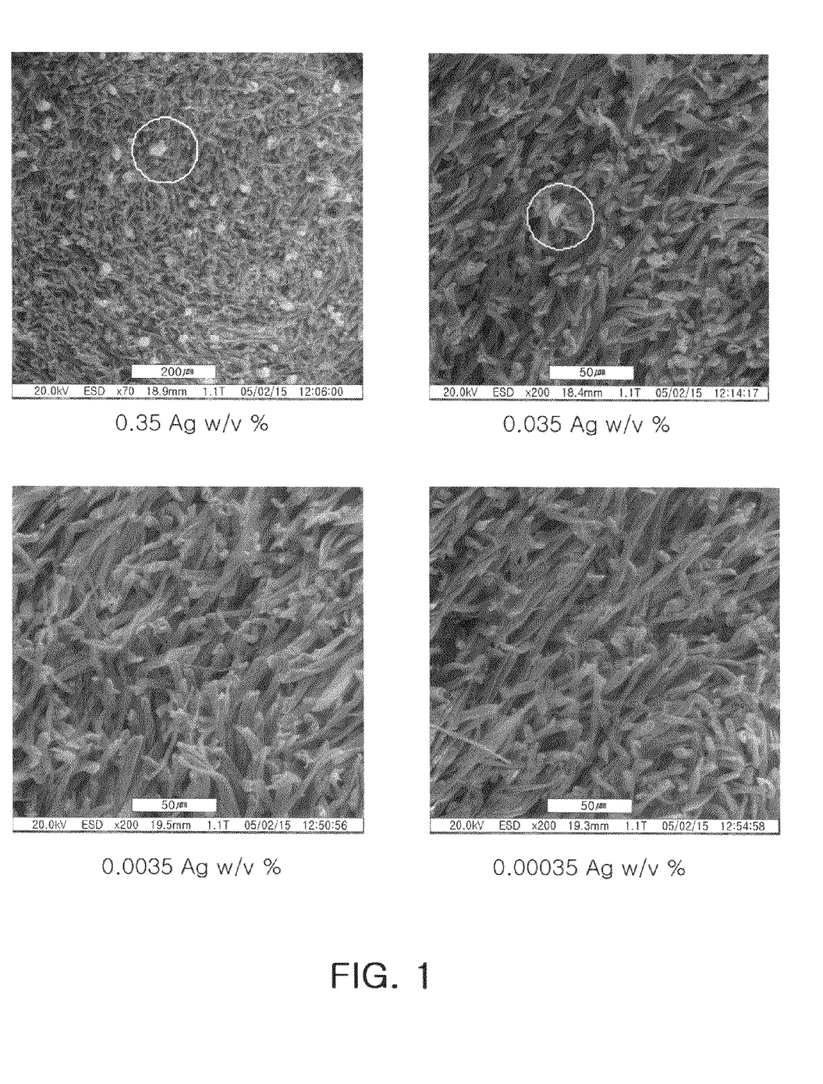
FIG. 1 is an ESEM photograph illustrating oral cotton pellets infused with different concentrations of silver.

FIG. 1 is an ESEM photograph illustrating a cotton having bonded silver. As shown in FIG. 1, when the silver was used in a concentration of 0.035 to 0.35 w/v %, silver crystals were detected on the cotton. However, the silver particles were not detected when the silver was used in a concentration 0.0035 w/v % or less.

Figure 2:
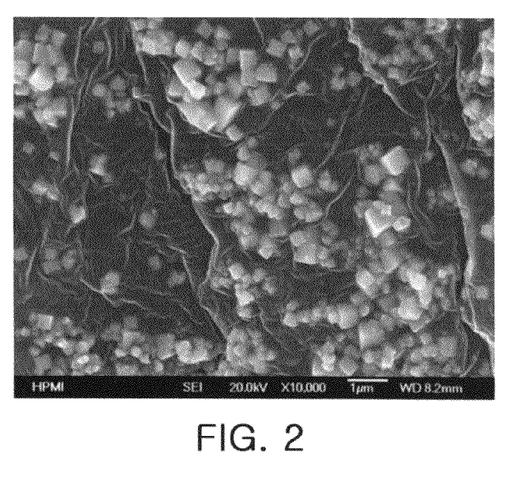
FIG. 2 is an ESEM photograph illustrating AgCl crystals.

The detected silver particles were silver crystals that did not chemically bind to cellulose. When the silver particles were converted into AgCl crystals, the converted AgCl crystals had a rectangular shape (see FIG. 2), and size of approximately 1 to 10 μm (micrometers). As a result, it was confirmed that the AgCl crystals might flow through blood vessels having a diameter of approximately 20 μm and be accumulated in the human body when the AgCl crystals were applied to human beings. When the silver is used in articles that are in direct contact with the human body, it is preferred to use the $NH_4OH$ solution having 0.035 w/v % or less of silver.

The components analysis was carried out using an energy dispersive x-ray analysis system (EDS). The distribution of each component obtained from the x-ray analysis system was displayed on the map, and concentrations of the components were derived from the EDS-Map analysis. As a result, the chemically bonded ionic silver was uniformly distributed over the surface of the cellulose matrix when the $NH_4OH$ solution having 0.0035 w/v % or less of silver was used. Also, the silver ions were not detected in a leaching test using water as a solvent. From these results, it was revealed that the ionic silver chemically binds to the cellulose by means of the mechanism represented by Equation 1.

2. Leaching Test

The cotton pellet having bonded silver thus prepared, paper media and a bandage were tested for whether silver is leached from the cotton pellet, the paper media and the bandage, by using an inductively coupled plasma (ICP, Perkin-Elmer Optima 3000DV) that was set to a relative limit of detection (LOD) of 0.9 ppb Ag so that it can read silver at a frequency of 328.068 nm.

The cotton pellet having bonded silver was stirred in 50 ml of deionized water at a rotary speed of 150 rpm for 24 hours. The resulting supernatant was tested for a concentration of residual silver using inductively coupled plasma mass spectrometry (ICP-MS). As listed in Table 1, it was revealed that silver ions or molecules are not detected.

As to the media used, a cotton pellet was used as the above-mentioned oral cotton pellet, and a round plate-type cotton paper filter that has been widely used in laboratories was used as the paper media. Also, a rectangular gauze that has been generally used for medical purposes was used as the bandage.

Concentration of silver, weight of media and total weight of silver in media were measured, as follows. Then, the results are listed in the following Table 1.

Concentration of silver: Each medium was dipped in 25 ml of conc. nitric acid ($HNO_3$) and 25 ml of hydrogen peroxide solution ($H_2O_2$), respectively, using a cooling machine. In this case small glass beads were used to disperse heat. Each solution was heated to a temperature at which bubbles generated in an initial reaction did not enter the cooling machine, and then additionally heated for 24 hours. The solid media were completely solubilized (digested), and a concentration of silver was measured using ICP-MS.

Weight of media: Before the experiments, the media were dried at 105° C. for 2 hours in a desiccator, and cooled to a room temperature. Then, dry weights of the media were measured.

Total weight of silver in media: the medium was diested, and each of the used solutions was evaporated. Then, distilled water was added to each of the solutions to correct the total amount of the solutions to 50 ml. Then, the concentration (mg/L) of silver measured with the ICP-MS was converted to an amount (mg) of silver, and the amount (mg) of silver was then divided by the weight of the medium. This may be represented by the following Equation.

Weight of silver=Concentration of silver (mg/L)×0.05 L)/Weight of media (g)

As listed in the following Table 1, the values of the control were obtained by measuring a concentration of silver present in a medium, which did not undergo the leaching test, by using a digestion method so as to compare to the leaching test. Also, the values after leaching were values obtained by stirring a medium for 24 hours at a rotary speed of 150 rpm in a solution using water as a solvent and measuring the concentration of silver present in the medium.

TABLE 1

| Media | Concentration of silver (mg/L) | Weight of media (g) | Total weight of silver in media (mg/g) | |
|---|---|---|---|---|
| | | | after leaching | Control |
| Cotton pellet | 6.846 | 0.7202 | 0.4752 | 0.4862 |
| Paper | 35.42 | 0.6288 | 2.8165 | 3.0453 |
| Bandage | 43.27 | 0.3463 | 6.2475 | 6.00245 |

As listed in Table 1, it might be seen that, when the weights of silver as measured before/after the leaching test are compared to each other, the measured values of the 3 media fall within the error range the analysis. From these results, it was revealed that the silver which chemically reacted with the natural cellulose according to the method of the present invention, was not leached from the natural cellulose when the natural cellulose was dispersed in water.

3. Culture of Microorganisms and Antimicrobial Test

*Candida albican*, *Micrococcus luteus*, *Pseudomonas putida*, and *Escherichia coli* were kindly provided by the American Type Culture Collection (ATCC). All the strains were cultivated at 37° C. for 24 hours in Luria broth (LB) media. The cultured cells of the strains were centrifuged to obtain cell pellets, and the cell pellets were washed twice with phosphate buffered saline (PBS). The cells were inoculated in 20 ml of PBS with an average level of approximately $10^4$ CFU/ml, and cultivated at 37° C. with the oral cotton pellet having chemically bonded silver or physically/chemically bonded silver, which was prepared in the $NH_4OH$ solution having an increasing concentration (0, 0.00035, 0.0035, 0.035, 0.35 and 0.7 w/v %) of silver. 48 hours after the cultivation, 1 ml of each cell sample was plated on an agar medium, and grown at 37° C. for 24 hours. The results are listed in the following Table 2. The cell density was measured using an agar plating method.

TABLE 2

| Microorganisms | Concentration of silver (w/v %) | | | | | |
|---|---|---|---|---|---|---|
| | 0 | 0.00035 | 0.0035 | 0.035 | 0.35 | 0.7 |
| *Candida albican* | >$10^4$ | ~$0.5 \times 10^4$ | 0 | 0 | 0 | 0 |
| *Micrococcus luteus* | >$10^4$ | 0 | 0 | 0 | 0 | 0 |
| *Pseudomonas putida* | >$10^4$ | 0 | 0 | 0 | 0 | 0 |
| *Escherichia coli* | >$10^4$ | ~$0.3 \times 10^3$ | 0 | 0 | 0 | 0 |

As listed in Table 2, it was revealed that *Micrococcus luteus* and *Pseudomonas putida* were not detected, but *Candida albican* and *Escherichia coli* were detected in the pellet prepared in the solution having 0.00035 w/v % of silver. Also, it was revealed that all the microorganisms were not detected in the pellet prepared in the solutions having more than 0.0035 w/v % of silver. Although not listed in Table 2, it was also revealed that the microorganisms were not detected in the pellet prepared in the solution having more than 0.7 w/v % of silver.

Figure 3:
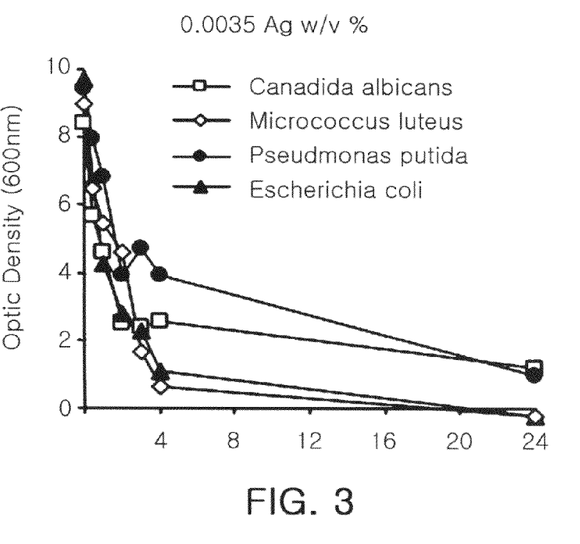
FIG. 3 is a graph illustrating the changes in concentration of four types of microorganisms with time as optical density values measured at 600 nm when the microorganisms are cultivated with the silver-infused oral cotton pellet (made from a solution including 0.0035 w/v % of silver)

FIG. 3 is a graph illustrating the changes in optical density at 600 nm for 4 types of microorganisms. In FIG. 3, it was shown that, when the microorganisms were cultured in the oral cotton pellet (0.0035 Ag w/v %) having chemically bonded silver, two microorganisms were reduced in number to 10% of the initial density of the microorganisms within 4 hours. Furthermore, it was shown that, when the other two microorganisms were cultivated in the oral cotton pellet having chemically bonded silver, the Optical Density values of *Pseudomonas putida* and *Candida albican* were not drastically reduced in number for two hours after cultivation, but finally reduced in number to 10% of the initial density of the microorganisms within 24 hours.

4. Culture of Human Cells and Cytotoxicity Test

Human alveolar epithelial cells (A549), which are morphologically similar to epithelial cells and derived from human lungs were kindly provided by the ATCC. The human alveolar epithelial cells were seeded with a density of $2 \times 10^4$ cells/cm$^2$ in a 24-well plate (Corning Costar) containing 10 ml of Dulbeco's Modified Eagle's Medium (DMEM) supplemented with 10% fetal bovine serum (FBS), L-glutamine (2 mM), amphotericin B (5.6 mg/L) and penicillin-streptomycin (100 U/ml).

Figure 4:
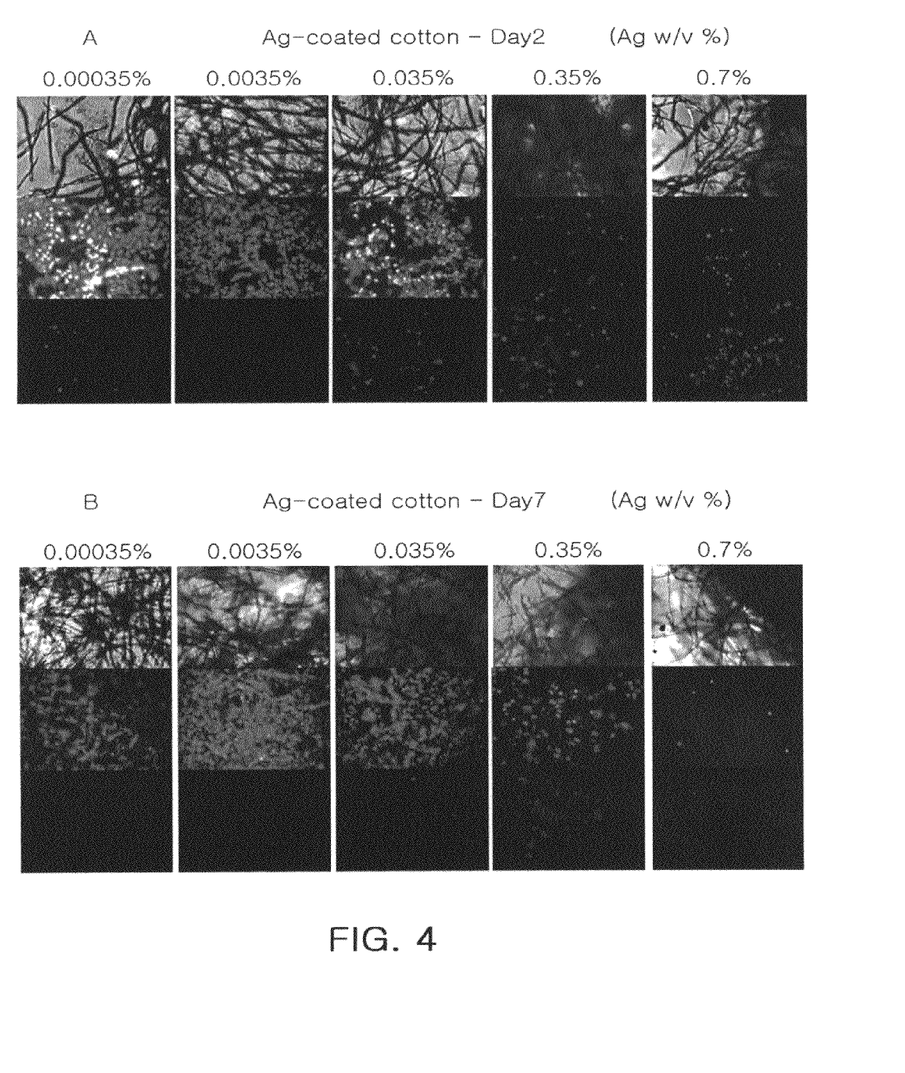
FIG. 4 sets A and B are photographs in color illustrating the correlation with the cytotoxicity of silver when human alveolar epithelial cells (A549) grow in each of the oral cotton pellets infused with different concentrations of silver.

As shown in FIG. 4, the human alveolar epithelial cell were grown in oral cotton pellets having an increasing concentration of physically and chemically bonded silver. The cytotoxicity of silver was monitored on days 1, 2 and 7. The effects of the oral cotton pellets having five different concentrations of bonded silver on cell viability and cytotoxicity were determined using a viability test kit (Molecular Probes, Eugene, Oreg.). On days 2 and 7, viable cells (green) were detected in the pellet prepared in the solution having 0.035 or less w/v % of silver, and dead cells (red) were mostly detected in the pellet prepared in the solution having 0.35 or more w/v % of silver. From these results, it was confirmed that cytotoxicity to human epithelial cells was not observed in the pellet prepared in the solution having 0.035 or less w/v % of silver.

5. Silver Leaching Test in Washing

The silver leaching test was carried out by washing socks and T-shirts which were made of cotton having 0.035% of physically and chemically bonded silver.

Each of cotton samples for the socks and T-shirts was cut into 200 regular tetragonal pieces with dimensions of 2 inches×2 inches. The 50 cotton samples were prepared, respectively. Then, each of the cotton samples was tested under conventional washing conditions without the use of a surfactant or synthetic detergent. The washing was carried out in a Hotpoint® washer.

Each of the cotton samples was put into a laundry bag, and the laundry bag was put into the washing machine. Then, each of the cotton samples was washed and spin-dried once. After washing, one of the samples was taken out of the laundry bag, and a concentration of silver in the sample was measured using an inductively coupled plasma ICP/digestion method. This method was carried out by taking out one sample after each washing and repeating the washing several times.

After each washing operation, the leaching behavior of silver, which was plotted in consideration of the initial concentration of silver in the sample, was recorded. The residual concentration of silver in each sample was measured using a ICP/digestion method, and compared with the initial concentration of silver to determine how much silver remained in each sample after washing. The results are listed in the following Table 3 and shown in FIG. 5.

TABLE 3

| Times of washing | Jockey pants | Socks |
| --- | --- | --- |
| 0 | 1.01 | 0.53 |
| 5 | 0.61 | 0.44 |
| 10 | 0.35 | 0.52 |
| 15 | 0.35 | 0.34 |
| 20 | 0.19 | 0.18 |
| 30 | 0.15 | 0.16 |

Unit: mg (Ag weight)/g (media weight)

When jockey pants, which are very thin underwear, were cut into sample pieces of 2 inches×2 inches, and the samples of the jockey pants were dipped in an NH$_4$OH solution having 0.035 w/v % of silver as listed in Table 3, the amount of the silver in the sample was 1.01 mg/g. When each of the samples was washed 20 times, the residual amount of silver was 0.19 mg/g, which accounted for approximately 20% of the initial concentration of silver, and the residual amount of silver was 0.15 mg/g, which accounted for approximately 15% of the initial concentration of silver, when each of the samples was washed 30 times.

The silver infused cotton showed antimicrobial activity even when content of silver in the matrix was approximately 0.01 mg/g after the silver was bound to the matrix in the NH$_4$OH solution having 0.00035 w/v % of silver. Therefore, the concentration of silver is sufficient to show antimicrobial activity after washing. The silver concentration was not decreased even after additional washing of the matrix, and was maintained to such a sufficient concentration that the silver can show antimicrobial activity, which indicates that the silver chemically binds to the cellulose.

Also, when the same concentration (i.e. 0.035 w/v %) of silver was in contact with cotton socks, the content of silver in the cotton socks was 0.53 mg/g, which was about half of the concentration of silver in the jockey pants. It was considered that this is because the reactivity of the silver was varied by the addition of other additives in the manufacture of the cotton socks. However, the content of silver in the cotton socks was substantially identical to that of the silver in the jockey pants when the cotton socks were washed 30 times.

Figure 5:
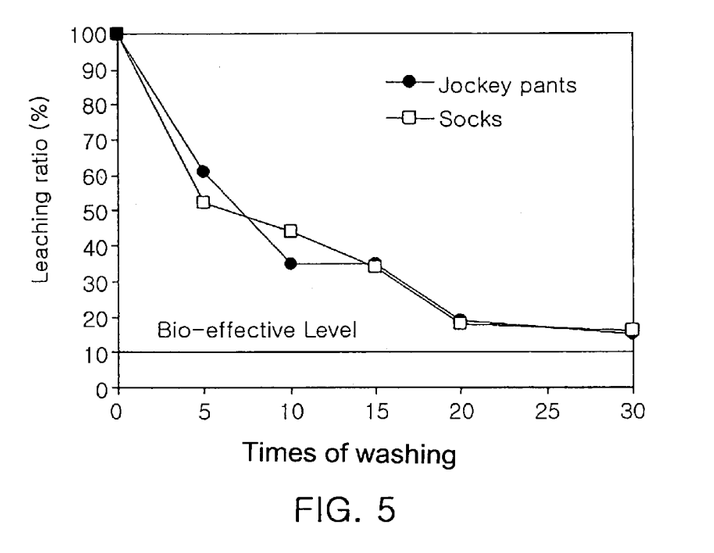
FIG. 5 is a graph illustrating the leaching ratio of silver in washing silver-containing products prepared according to one exemplary embodiment of the present invention.

In addition, as shown in FIG. 5, it was revealed that silver was detached from the samples until the samples were washed 20 times. However, it was considered that the detached silver was derived from the cellulose-OAg broken by physical forces, and silver components physically bonded to the matrix.

Meanwhile, in case these experimental results were compared to the leaching test results of Example 2 as listed in Table 1, silver was not leached from the sample of Example 2 when the sample was stirred at a rotary speed of 150 rpm for 24 hours. However, it was shown that, when the physical forces were high as in the washing and spin-drying of the washing machine, the silver components physically bonded to the matrix were also leached from the matrix. However, the above two cases show that the silver, which was bonded to cellulose according to the method of the present invention was not leached from the cellulose but maintained sufficient antimicrobial activity when the cellulose matrix was dispersed in water.

The invention claimed is:

1. A method for preparing an antimicrobial cotton of natural cellulose matrix having chemically bonded silver, the method comprising:
   introducing silver ions ($Ag^+$) into a natural cellulose matrix by dipping the natural cellulose matrix in a solution consisting of AgCl dissolved in $NH_4OH$; and
   substituting hydrogen (H) of hydroxyl group (—OH) in cellulose with $Ag^+$ by drying the silver ion-infused natural cellulose matrix, thus to form a cellulose-OAg complex having a chemical bond.

2. The method of claim 1, wherein a concentration of silver in the $NH_4OH$ solution is in a range of 0.00035 to 0.0035 Ag w/v %.

3. A method for preparing an antimicrobial cotton of natural cellulose matrix having chemically and/or physically bonded silver, the method comprising:
   introducing silver ions ($Ag^+$) into a natural cellulose matrix by dipping the natural cellulose matrix in a solution consisting of AgCl dissolved in $NH_4OH$; and
   substituting hydrogen (H) of hydroxyl group (—OH) in cellulose with $Ag^+$ by drying the silver ion-infused natural cellulose matrix, thus to form a cellulose-OAg complex having a chemical bond and a physical bond between cellulose and silver molecules or between silver particles of silver oxide ($Ag_2O$).

4. The method of claim 3, wherein a concentration of silver in the $NH_4OH$ solution is in a range of 0.0035 to 7.5 Ag w/v %.

5. The method of claim 1, wherein the operation of introducing silver ions ($Ag^+$) into a natural cellulose matrix is carried out for 1 to 96 hours.

6. The method of claim 2, wherein the operation of introducing silver ions ($Ag^+$) into a natural cellulose matrix is carried out for 1 to 96 hours.

7. The method of claim 3, wherein the operation of introducing silver ions ($Ag^+$) into a natural cellulose matrix is carried out for 1 to 96 hours.

8. The method of claim 4, wherein the operation of introducing silver ions ($Ag^+$) into a natural cellulose matrix is carried out for 1 to 96 hours.

9. The method of claim 1, wherein the drying temperature is in a range of 100 to 150° C.

10. The method of claim 2, wherein the drying temperature is in a range of 100 to 150° C.

11. The method of claim 3, wherein the drying temperature is in a range of 100 to 150° C.

12. The method of claim 4, wherein the drying temperature is in a range of 100 to 150° C.

13. An antimicrobial cotton of natural cellulose matrix having chemically and/or physically bonded silver, wherein the natural cellulose matrix is prepared in the method defined in any of claim 1 and has a chemical bond of a cellulose-OAg complex, or a chemical bond of a cellulose-OAg complex and a physical bond between particles of silver oxide ($Ag_2O$) in cellulose, the cellulose-OAg complex being formed by substituting hydrogen (H) of hydroxyl group (—OH), which is present in the $3^{rd}$ carbon of the glucose units, with $Ag^+$ by drying the silver ion-infused natural cellulose matrix.

14. An antimicrobial cotton of natural cellulose matrix having chemically and/or physically bonded silver, wherein the natural cellulose matrix is prepared in the method defined in claim 2 and has a chemical bond of a cellulose-Oag complex, or a chemical bond of a cellulose-OAg complex and a physical bond between particles of silver oxide ($Ag_2O$) in cellulose, the cellulose-OAg complex being formed by substituting hydrogen (H) of hydroxyl group (—OH), which is present in the $3^{rd}$ carbon of the glucose units, with $Ag^+$ by drying the silver ion-infused natural cellulose matrix.

15. An antimicrobial cotton of natural cellulose matrix having chemically and/or physically bonded silver, wherein the natural cellulose matrix is prepared in the method defined in claim 3 and has a chemical bond of a cellulose-OAg complex, or a chemical bond of a cellulose-OAg complex and a physical bond between particles of silver oxide ($Ag_2O$) in cellulose, the cellulose-OAg complex being formed by substituting hydrogen (H) of hydroxyl group (—OH), which is present in the $3^{rd}$ carbon of the glucose units, with $Ag^+$ by drying the silver ion-infused natural cellulose matrix.

16. An antimicrobial cotton of natural cellulose matrix having chemically and/or physically bonded silver, wherein the natural cellulose matrix is prepared in the method defined in claim 4 and has a chemical bond of a cellulose-OAg complex, or a chemical bond of a cellulose-OAg complex and a physical bond between particles of silver oxide ($Ag_2O$) in cellulose, the cellulose-OAg complex being formed by substituting hydrogen (H) of hydroxyl group (—OH), which is present in the $3^{rd}$ carbon of the glucose units, with $Ag^+$ by drying the silver ion-infused natural cellulose matrix.

* * * * *

UNITED STATES PATENT AND TRADEMARK OFFICE
CERTIFICATE OF CORRECTION

| | |
|---|---|
| PATENT NO. | : 8,293,267 B2 |
| APPLICATION NO. | : 12/456162 |
| DATED | : October 23, 2012 |
| INVENTOR(S) | : Ju Young Kim |

Page 1 of 1

It is certified that error appears in the above-identified patent and that said Letters Patent is hereby corrected as shown below:

Column 12, Line 18, Claim 14, delete "cellulose-Oag" and insert -- cellulose-OAg --

Signed and Sealed this
First Day of January, 2013

David J. Kappos
*Director of the United States Patent and Trademark Office*